United States Patent [19]

Kympl

[11] Patent Number: 4,471,784

[45] Date of Patent: Sep. 18, 1984

[54] SOURCE OF PULSES FOR ELECTRONIC SUPPRESSION OF PAIN

[75] Inventor: Vladislav Kympl, Liberec, Czechoslovakia

[73] Assignee: TESLA koncernovy podnik, Prague, Czechoslovakia

[21] Appl. No.: 442,109

[22] Filed: Nov. 16, 1982

[30] Foreign Application Priority Data

Apr. 6, 1981 [CS] Czechoslovakia .................... 2560-81

[51] Int. Cl.³ .............................................. A61N 1/36
[52] U.S. Cl. ................................. 128/422; 331/113 R
[58] Field of Search ............ 128/419 R, 419 E, 419 F, 128/419 G, 419 PG, 419 D, 419 S, 419 C, 421–422; 331/108 A, 110, 113 R, 144

[56] References Cited

U.S. PATENT DOCUMENTS

| | | | |
|---|---|---|---|
| 3,563,247 | 2/1971 | Bowers | 128/419 PG |
| 3,595,242 | 7/1971 | Berkovits | 128/419 PG |
| 3,596,146 | 7/1971 | McDonald | 331/113 R |
| 3,713,449 | 1/1973 | Mulier | 128/422 |
| 3,746,006 | 7/1973 | Thaler | 128/421 |
| 3,867,949 | 2/1975 | Schwalm et al. | 128/422 |
| 3,971,389 | 7/1976 | Brownlee et al. | 128/419 PG |
| 4,261,365 | 4/1981 | Nordling | 128/419 PG |
| 4,298,007 | 11/1981 | Wright et al. | 128/419 PG |

FOREIGN PATENT DOCUMENTS 1190030  4/1965  Fed. Rep. of Germany ... 331/113 R

Primary Examiner—William E. Kamm
Assistant Examiner—Mitchell J. Shein

[57] ABSTRACT

A source of pulses for the electronic suppression of pain is represented by a multivibrator wherein the amplitude of the output signal is double the value of the feeding voltage. The principle of the invention resides in a multivibrator provided with two sets of complementary pairs of transistors, one set of which works simultaneously as a switch and a feeder of voltage doublers. The multivibrator is fed by this increased voltage so that at the output, pulses of double amplitude arise, i.e. an amplitude four times greater than the value of the feeding voltage.

1 Claim, 1 Drawing Figure

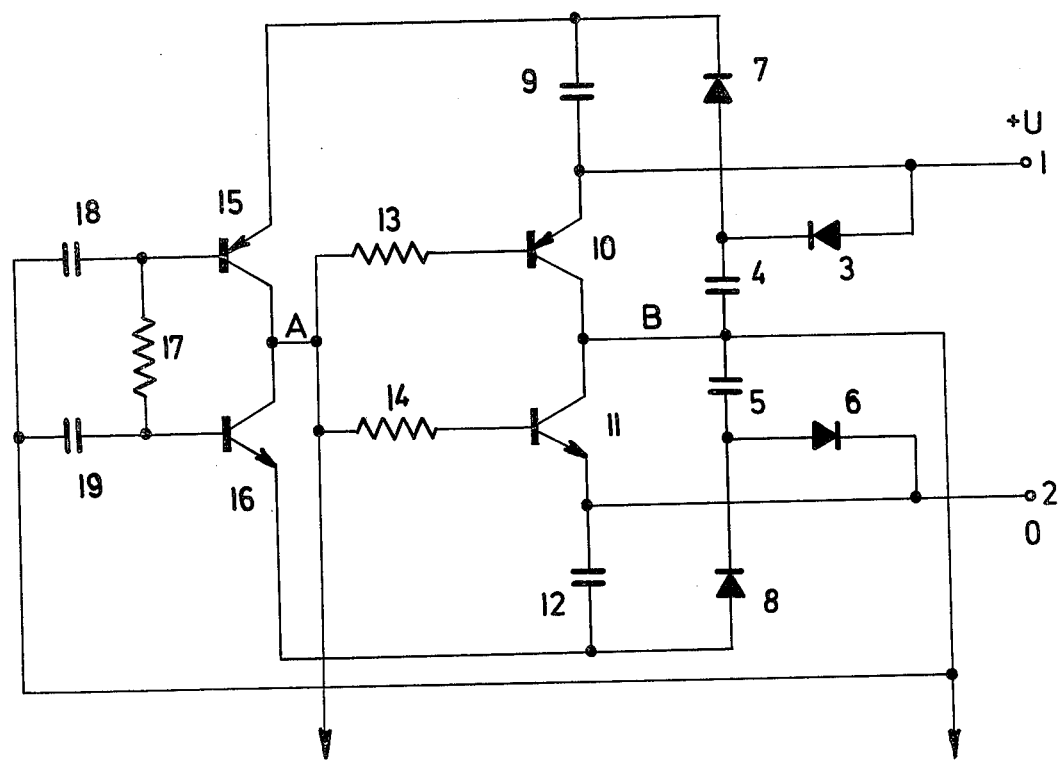

SOURCE OF PULSES FOR ELECTRONIC SUPPRESSION OF PAIN

BACKGROUND OF THE INVENTION

The invention relates to a source of pulses for electronic instruments designed for suppression of pain.

There are known instruments, which provide oscillations of a frequency from 10 Hz up to 2000 Hz, with a voltage around 30 V, the principle of which resides in the fact that after output electrodes have been applied on the skin of a patient—at least one of the electrodes being situated in the respective active spot—there appears to be an analgetic effect, i.e. phantom pains are either diminished or suppressed completely.

As to the design of these known instruments, a source of oscillation is mostly represented by a multivibrator having excitation voltages of 30 V and more, or with other additional circuits, transformers, etc. This fact makes the requirements for a supply source and dimensions of the instrument more complicated.

SUMMARY OF THE INVENTION

The abovementioned drawback may be obviated by wiring a multivibrator with a double amplitude of the output signal according to the invention, the principle of which resides in the fact that in parallel to the input terminals, there are connected both a serial combination of a first charging diode, first and second charging capacitors and a second charging diode, as well as the emitters of a first complementary pair of transistors, the collectors thereof being connected to a common point B of the first and second charging capacitors, while the bases thereof are connected through exciting resistors to a common point A of the collectors of a second complementary pair of transistors, the emitters of which being connected through respective diode gates and the charging diodes, shunted by a first and second smoothing condenser, to the input terminals, the bases of the second complementary pair of transistors being interconnected by means of a charging resistor and connected through respective coupling condensers to the common point B of the collectors of the first complementary pair of transistors and charging capacitors.

The wiring according to the invention is in fact a multivibrator with two pairs of complementary transistors, one pair of which also works as a change-over switch and feeder of the voltage doublers, working in the rhythm of the multivibrator. If we do not take into consideration voltage drops in the semiconductor junctions, then the amplitude in the output of the multivibrator at a common points A and B is four times greater than the supply voltage of the source.

DESCRIPTION OF THE DRAWING

In order that the invention may be clearly understood and readily carried into effect, a preferred embodiment thereof is, by way of example, hereinafter more fully described and illustrated in the accompanying drawing, in which:

FIG. 1 shows a wiring diagram of the multivibrator according to the invention.

DESCRIPTION OF THE PREFERRED EMBODIMENT

Referring to the FIGURE, in parallel to input terminals 1 and 2, there are connected a serial combination of a first charging diode 3, a first charging capacitor 4, a second charging capacitor 5, a second charging diode 6, and a first complementary pair of transistors 10 and 11, the emitters of which being connected to the input terminals 1, 2, respectively, and the collectors of which being connected to a common point B of the first and second charging capacitors 4 and 5. The bases of the first complementary pair of transistors 10, 11 are connected, through respective feeding resistors 13, 14, to a common point A, to which the collectors of a second complementary pair of transistors 15 and 16 are respectively connected. The emitters of the second complementary pair of transistors 15, 16 are respectively connected, through diode gates 7 and 8 and the charging diodes 3, 6, shunted by first and second smoothing condensers 9 and 12, to the input terminals 1, 2. The bases of the second complementary pair of transistors 15, 16 are mutually connected by means of a shunting charging resistor 17, and by means of respective coupling condensers 18 and 19, which in turn are connected to the common point B of the first and second charging capacitors 4, 5 and the collectors of the first complementary pair of transistors 10, 11.

After connecting the source of supply voltage to terminals 1 and 2, one of the transistors 15 or 16 starts opening more quickly than the other. Let us assume that it is transistor 15. So, in the common point A of the collectors of transistors 15 and 16, a positive voltage of the source appears. Voltage drops in the semiconductor junctions may be neglected for making the case simpler. The positive voltage in the common point A causes the closing of the transistor 10 and the opening of the transistor 11. In this way the common point B of the collectors of transistors 10 and 11 and the charging capacitors 4 and 5 is connected to the zero potential terminal 2 of the supply voltage, and the capacitor 4 is charged to the full voltage of the source through the charging diode 3.

As the coupling condensers 18 and 19 are also connected to the common point B, which is now connected to the zero potential terminal 2, the coupling condenser 18 will be charged by the base-emitter path of the transistor 15, and, through the charging resistor 17, the coupling condenser 19 will be charged as well.

The positive voltage across the bases of the transistors 15 and 16 causes a change of their conductivity. The transistor 15 closes while the transistor 16 opens and, in this way, connects the common point A of the collectors of the transistors 15 and 16 to the zero potential terminal 2 of the supply voltage source. This fact causes the opening of the transistor 10 and the closing of the transistor 11. The common point B of the collectors of the transistors 10 and 11 and of the charging capacitors 4 and 5 has now the same potential as the positive terminal 1 of the source. As the charging capacitor 4 was charged in advance, the voltage between the positive end of capacitor 4 and the zero potential terminal 2 is doubled with respect to the voltage of the source. The smoothing condenser 9 is fed with this voltage through the diode gate 7.

Simultaneously, the capacitor 5 is charged through the charging diode 6 and the coupling condenser 19 is discharged through the base-emitter path of the transistor 16; through the resistor 17, there is discharged the coupling condenser 18. The discharging of the coupling condensers 18 and 19 causes again a change of conductivity of the transistors. The transistors 15 and 11 open, the transistors 16 and 10 close. At the common point A, the potential is identical with the potential of the positive end of the smoothing condenser 9, viz. it is higher than the voltage of the supply source.

The common point B is connected again to the zero potential terminal 2. The charging capacitor 4 is charged again through the diode 3 to the voltage of the source. The charging capacitor 5 is discharged through the diode gate 8 into the smoothing condenser 12. Simultaneously, the coupling condenser 18 is charged through the base-emitter path of transistor 15 and the coupling condenser 19 through the charging resistor 17. The charging of these condensers causes again the change of conductivity of the transistors 15 and 16 and the process repeats in the described way. The smoothing condensers 9 and 12 are charged continuously up to the full voltage of the source. At the positive end of the smoothing condenser 9, the voltage is doubled with respect to the zero potential terminal, and at the negative end of the smoothing condenser 12, there is the same voltage, but of the opposite polarity than the voltage of the supply source. Across the mentioned ends, the voltage is tripled with respect to the supply source.

Between the common points A and B, rectangular voltage pulses arise. If one marks the supply voltage U and if one neglects the voltage drops in the semiconductor junctions, then in case of conductivity of transistors 15 and 11, at the common point A, a voltage of +2U takes place, and at the common point B there is zero voltage. In case of conductivity of the transistors 16 and 10, a voltage −U takes place at the common point A, and a voltage +U at the common point B.

The change of these pulses is determined by the time constant of the coupling condensers 18 and 19 and the charging resistor 17.

The wiring may be carried out even with an opposite polarity of semiconductor elements, condensers and supply voltage.

The invention may be applied for portable battery instruments, where one needs voltage pulses, the amplitude of which is a multiple of the feeding voltage of ordinary batteries, e.g. portable embodiments of instruments for electric acupuncture.

Although the invention is illustrated and described with reference to one preferred embodiment thereof, it is to be expressly understood that it is in no way limited to the disclosure of such a preferred embodiment, but it is capable of numerous modifications within the scope of the appended claims.

What we claim is:

1. A source of pulses for the electronic suppression of pain, said source comprising input terminals, a serial combination of a first charging diode, a first and a second charging capacitor and a second charging diode, a first complementary pair of transistors, the emitters of which and said serial combination both being in parallel with said input terminals, the collectors of said first complementary pair of transistors being coupled to a first common point of said first and second charging capacitors, a pair of exciting resistors, a second complementary pair of transistors, the collectors thereof being interconnected at a second common point, to which the basis of said first complementary pair of transistors are each connected through a respective one of said pair of exciting resistors, the emitters of said second complementary pair of transistors being coupled through respective diode gates and said first and second charging diodes, respectively, shunted respectively by a first and a second smoothing condenser, to said input terminals, a charging resistor shunting the bases of said second complementary pair of transistors, and a pair of coupling condensers respectively connecting the bases of said second complementary pair of transistors to said first common point.

* * * * *